(12) United States Patent
Nanko et al.

(10) Patent No.: US 7,279,106 B2
(45) Date of Patent: *Oct. 9, 2007

(54) ADSORBENT AND METHOD FOR ADSORBING A CHEMOKINE IN BODY FLUID

(75) Inventors: Toshiki Nanko, Kobe (JP); Shigeo Furuyoshi, Kobe (JP); Satoshi Takata, Takasago (JP); Masaru Nakatani, Settsu (JP)

(73) Assignee: Kaneka Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/067,748

(22) Filed: Mar. 1, 2005

(65) Prior Publication Data

US 2005/0145573 A1 Jul. 7, 2005

Related U.S. Application Data

(60) Division of application No. 10/623,735, filed on Jul. 22, 2003, now Pat. No. 6,878,269, which is a continuation-in-part of application No. 08/930,271, filed as application No. PCT/JP97/00254 on Jan. 30, 1997, now abandoned.

(30) Foreign Application Priority Data

Jan. 31, 1996 (JP) .................... 8-15502
Mar. 28, 1996 (JP) .................... 8-74721

(51) Int. Cl.
*B01D 15/00* (2006.01)
(52) U.S. Cl. .............. 210/679; 210/691; 530/415
(58) Field of Classification Search ........... 210/679, 210/691, 692, 502.1; 502/401, 402, 405; 530/351, 412, 415, 416, 417
See application file for complete search history.

(56) References Cited

U.S. PATENT DOCUMENTS 4,476,023 A 10/1984 Horikoshi et al. .......... 210/446

(Continued)

FOREIGN PATENT DOCUMENTS

EP    0 247 592 A2    12/1987

(Continued)

OTHER PUBLICATIONS

F. Gejyo et al., "A New Form of Amyloid Protein Associated with Chronic Hemodialysis was Identified as $\beta_2$-Microglobulin", *Biochemical and Biophysical Research Communicatios*, vol. 129, No. 3, pp. 701-706 (1985).

(Continued)

*Primary Examiner*—Peter A. Hruskoci
(74) *Attorney, Agent, or Firm*—Kubovcik & Kubovcik

(57) ABSTRACT

A device for body fluid purification, comprising a container having an inlet and an outlet for a fluid and a means for preventing an adsorbent from flowing out of the container and an adsorbent charged in the container, the adsorbent comprising a spherical hydrogel, the spherical hydrogel having an average particle size in a range of from about 460 to 600 μm and having a substantially uniform particle size and comprising an epoxidated cellulose having hexadecylamine immobilized thereon in an amount of 100 to 300 μmol per gram of dry weight of said epoxidated cellulose, and water, wherein the weight ratio of said epoxidated cellulose having hexadecylamine immobilized thereon to the water is 2:8.

7 Claims, 5 Drawing Sheets

U.S. PATENT DOCUMENTS

| | | | |
|---|---|---|---|
| 4,721,730 A | 1/1988 | Furuyoshi et al. | 521/53 |
| 4,744,899 A | 5/1988 | Tani et al. | 210/263 |
| 4,770,774 A | 9/1988 | Ida et al. | 210/259 |
| 5,700,372 A | 12/1997 | Takesawa et al. | 210/500.23 |
| 5,919,898 A * | 7/1999 | Nakatani et al. | 530/345 |
| 6,303,153 B1 * | 10/2001 | Friedland et al. | 424/529 |
| 6,559,290 B1 * | 5/2003 | Nakatani et al. | 530/415 |
| 2004/0253604 A1 * | 12/2004 | Lin et al. | 435/6 |

FOREIGN PATENT DOCUMENTS

| | | |
|---|---|---|
| EP | 0 265 924 A2 | 5/1988 |
| EP | 0 723 794 A | 7/1996 |
| JP | 61-100262 A | 5/1986 |
| JP | 63-77 457 A | 4/1988 |
| JP | 63-99 875 A | 5/1988 |
| JP | 63-117039 A | 5/1988 |
| JP | 2-180273 A | 7/1990 |
| JP | 5-170799 A | 7/1993 |
| JP | 6-312 017 A | 11/1994 |
| JP | 6-312 134 A | 11/1994 |
| JP | 8-257 398 A | 10/1996 |

OTHER PUBLICATIONS

M. Baggiolini et al., "CC Chemokines in Allergic Inflammation", *Immunology Today*, vol. 15, No. 3, pp. 127-133, (1994).

J. Chihara, *Clinical Immunology*, vol. 27 (Suppl. 16): pp. 162-171, 1995 (with partial English translation).

K. Matsushima, *Clinical Immunology*, vol. 27 (Suppl. 16): pp. 147-154, 1995 (with partial English translation).

N. Sekido et al., "Prevention of Lung Reperfusion Injury in Rabbits by a Monoclonal Antibody Against Interleukin-8", *Nature*, 365, pp. 654-657 (1993).

S. Endo et al., *Intensive & Critical Care Medicine*, 4(12), pp. 1357-1365, 1992 (with partial English translation).

H. Inoue et al., "Expression of Inflammatory Cytokines and Adhesion Molecules in Haemodialysis-assocaited Amyloidosis", *Nephrol Dial Transplant*, 10, pp. 2077-2082 (1995).

K. Matsushima, "Property and Relationship to Inflamatory Diseases", *Menekiyakuri*, vol. 12, No. 1, pp. 15-21, 1994.

*The Cytokine Data Manual*, Edit. by Dept. of Microbiology, Kyoto Prefectural University of Medicine, Nankodo, pp. 105-108, 1995 (with partial English translation).

A. Leo et al., "Partition Coefficients and Their Uses", *Chemical Reviews*, vol. 71, No. 6, pp. 525-616 (1971).

R. Rekker, "The Hydrophobic Fragmental Constant", *Pharmacochemistry Library*, Elsevier Sci. Pub. Comp., vol. 1, Chp. 3, pp. 39-107 (1977).

S. Endo et al., *Intensive & Critical Care Medicine*, 6(2), pp. 115-123, 1994 (with partial English translation).

H. Hirasawa et al., *Intensive & Critical Care Medicine*, 6(2), pp. 105-114, 1994 (with partial English translation).

S. Furuyoshi et al., "New Absorbents for Extracorporeal Removal of $B_2$-Microglobulin", *Amyloid and Amyloidosis*, Edit. by T. Isobe et al., Plenum Publishing Corp., pp. 629-634 (1988).

F. Gejyo et al., "Long-Term Clinical Evaluation of an Adsorbent Column (BM-01) of Direct Hemoperfusion Type for $\beta_2$-Microglobulin on the Treatment of Dialysis-Related Amyloidosis", *Artificial Organs*, 19(12), pp. 1222-1226 (1995).

* cited by examiner

ADSORBENT AND METHOD FOR ADSORBING A CHEMOKINE IN BODY FLUID

CROSS-REFERENCE TO RELATED APPLICATION

This application is a division of application Ser. No. 10/623,735, filed Jul. 22, 2003, now U.S. Pat. No. 6,878,269 which is a continuation-in-part of application Ser. No. 08/930,271 filed on Sep. 29, 1997,abandoned, which is a 371 of PCT/JP97/00254, filed Jan. 30, 1997.

This application claims priority based on Japanese patent application Nos. 1996-15502 and 1996-74721 filed Jan. 31 and Mar. 28, 1996, respectively, which are incorporated herein by reference.

TECHNICAL FIELD

This invention relates to an adsorbent for removing substances related to malady in body fluid such as blood, especially small molecular weight proteins including β2-microglobulin and chemokines, etc., a method for removing substances related to malady in body fluid by using said adsorbent, a device for body fluid purification and a system for body fluid purification.

BACKGROUND ART

In this quarter of a century, a body fluid purifying technology by an extracorporeal circulation, especially a blood purifying technology, has accomplished a remarkable progress.

Above all, hemodialysis has been widespread as a blood purifying method that executes a kidney function of a renal insufficient patient. A principle of this hemodialysis lies in that blood and dialysate are contacted with each other through a dialysis membrane and body wastes in blood are discharged to dialysate by a difference in concentration of solute between both liquids. Various hemodialyzers which use a plate-type or hollow fiber-type membrane, etc. have been developed and used clinically.

Hemofiltration or hemodiafiltration are also used as a blood purification method that uses a membrane as in hemodialysis.

On the other hand, various blood purification methods that use adsorbents are examined, and, an adsorber which is used to assist a kidney function and charged with a granular active carbon is on the market.

In recent years, in a field of hemodialysis, it becomes an issue that small molecular weight proteins accumulate in blood of a renal insufficient patient who undergo a hemodialysis therapy. It is generally thought that this accumulation occurs because these small molecular weight proteins, which should be metabolized with a kidney in a normal state, cannot be removed by a conventional hemodialyzer.

As an example of such small molecular weight proteins, β2-microglobulin is given, which is a protein constituting an amyloid deposition of a dialysis-related amyloidosis patient as revealed in 1985 by Gejyo et al. The molecular weight of β2-microglobulin is reported to be 11,731 (F. Gejyo et al., Biochemical and Biophysical Research Communications, Vol. 129, No. 3, Pages 701-706, 1985).

In order to improve the performance of removing such a small molecular weight protein, a means of enlarging the pore size of hemodialysis membrane is used, and a hemodialyzer using the so-called high performance membrane has been developed and used clinically, but, at present, it is hard to say that enough removing performance is accomplished.

Also it becomes possible to remove these small molecular weight proteins in a considerably high efficiency by a hemofiltration method or a hemodiafiltration method, but problems lie in points that these methods need quite a large quantity of fluid replacement which a usual hemodialysis does not need and that an additional equipment is necessary to a dialysis control machine used widely.

Further, in methods using these membranes, it becomes an anxious issue that there occurs pollution by toxic substances such as an endotoxin of a bacterium, etc. from the dialysate side, which accompanies enlarged pore size of membranes.

On the other hand, the adsorber which is charged with a granular active carbon is not originally designed for adsorption of proteins, and is poor in adsorbing ability for small molecular weight proteins, and it is the present situation of the adsorber that a sufficient removal of these proteins cannot be performed.

On the other hand, an immunocompetent cell produces various kinds of active substances when causing immune response. A part thereof is a proteinaceous substance called cytokine and plays a greatly important role as a biophylactic factor which is closely related to various kinds of antigen-specific or non-specific inflammatory responses. Essentially, cytokine is necessary and indispensable for maintaining biological homeostasis and is produced excessively in pathological conditions such as inflammation and the like, relating to the formation and prolongation of inflammation and the like.

Among the cytokines, especially, ones having chemotaxis are generically named chemokines. Chemotaxis is also referred to as chemotropism, and means tropism caused by difference in concentration of a chemical entity. It is known that the substances referred to as chemokines form one family for their structural characteristics.

Chemokines are characterized in that they exist mainly as proteins having a molecular weight of from about 6,000 to about 10,000. Depending on the kind of chemokines, however, there exist chemokines which form dimers or tetramers in fluid, and chemokines having a molecular weight more than 10,000 because of O-glycosylation. Also, chemokines are classified into the following two subfamilies according to their structural characteristics. One is CXC subfamily, and the other is CC subfamily. As shown in a Review of M. Baggiolini et al, "CC CHEMOKINES IN ALLERGIC INFLAMMATION", Immunology Today, 15, 127, 1994, a chemokine has four cysteine residues (hereinafter a cysteine residue is referred to as C) in a position firmly conserved in its molecule. When such four Cs are referred to as C1, C2, C3 and C4 in that order from N-terminus, CXC subfamily is that wherein one optional amino acid (hereinafter referred to as X) exists between C1 and C2, and CC subfamily is that wherein no amino acid exists between C1 and C2. Further, it is shown that chemokines in each subfamily have homology in a sequence of amino acids other than Cs (e.g., Chihara's report, Clinical Immunology, 27 [Suppl. 16], 162-171, 1995).

It has been thought that CXC subfamily acts mainly on a neutrophil among leukocytes, while CC subfamily acts mainly on a monocyte, an eosinophil, a basophil and a lymphocyte among leukocytes. Recently, however, it has been suggested that they exert their effects on various kinds of cells. For instance, it is known that interleukin-8 shows physiological activities on a lymphocyte, a basophil, an eosinophil, an epidermal keratinocyte, a melanomatous cell, a fibroblast and an endothelial cell as well as a neutrophil, although interleukin-8 is an interleukin having chemotaxis among interleukins and is a chemokine belonging to CXC subfamily (Matsushima, Clinical Immunology, 27 [Suppl. 16], 147-154, 1995).

Further, it is known that, for instance, on a human monocyte, there exist not only receptors specific to each of monocyte chemoattractant protein-1 (hereinafter referred to as MCP-1) and macrophage inflammatory protein-1 (hereinafter referred to as MIP-1) which are chemokines belonging to CC subfamily, but also a common receptor specific to three kinds of chemokines belonging to CC subfamily, i.e., MCP-1, MIP-1 and RANTES (Regulated upon Activation in Normal T cells Expressed and Secreted) (Matsushima, Clinical Immunology, 27 [Suppl. 16], 147-154, 1995). This finding suggests that there exist chemokines in one subfamily which exert the same physiological activity through the same receptor.

Once a living body has stress or infection from the outside, inflammation is caused as a biophylactic response, and there arises infiltration of leukocytes into an inflammatory site. Such infiltration of leukocytes into an inflammatory site is caused by leukocyte chemotactic factor produced at the inflammatory site. It is known that a chemokine plays a role as a causative factor of the infiltration of leukocytes. In fact, it has been demonstrated that in an acute inflammation model in rabbit, administration of an antibody against interleukin-8 (anti-IL-8-antibody) being one of chemokines blocks infiltration of neutrophilics at a inflammatory site and inhibits a disorder of organ accompanying acute inflammation (Sekido et al., Nature, 365, 654-657, 1993).

Furthermore, recently it has been reported that a network of cytokines is activated by overproduction of various cytokines, and the induction and activation of neutrophils are caused by overproduction of chemokines due to the activation of the network of cytokines, in pathological conditions included in a conception of systemic inflammatory response syndrome (SIRS) (Endo et al., Intensive & Critical Care Medicine, 4, 1357-1365, 1992). It is suggested that these progress systemic inflammatory response, and shock, a tissue disorder and pluriorganic insufficiency are caused, and then death may come.

It is suggested that at a pathologic site with allergic inflammation, various inflammatory cells such as a lymphocyte and an eosinophil infiltrate by action of chemokines such as RANTES, platelet factor-4 (hereinafter referred to as PF-4) and macrophage inflammatory protein-1α (hereinafter referred to as MIP-1α), as key substances.

Also, for instance, in case of carrying out blood extracorporeal circulation such as dialysis therapy, the possibility has been suggested that chemokines are overproduced by stimulation to an immunocompetent cell by means of contact with an artificial material, irritants of which typical example is microbial endotoxin in dialysate, various irritant factors existing in blood or tissue, and the like. For instance, in dialysis amyloidosis or carpal tunnel syndrome which is a complication accompanying a long-term dialysis therapy, the possibility has been suggested that MCP-1 or MIP-1α is overproduced and relates to formation of pathological, conditions (Inoue et al., Nephrology Dialysis Transplantation, 10, 2077-2082, 1995).

Further, an abnormally high concentration of interleukin-8 being one of chemokines has been detected at an inflammatory site or in peripheral blood of patients with diseases such as gouty arthritis, psoriasis, contact dermatitis, idiopathic fibroid lung, adult respiratory distress syndrome, inflammatory bowel disease, immune angiitis, urinary tract infection, cardiac infarction, asthma, respiratory tract infection, perinatal infectious disease and rejection in organ transplantation, as compared with a normal human (Menekiyakuri, 12, No. 1, 15-21, 1994).

Also, there abnormally appear interleukin-8, RANTES, MCP-1, MIP-1α and macrophage inflammatory protein-1β (hereinafter referred to as MIP-1β) in rheumatoid arthritis; MCP-1, MIP-1α and MIP-1β in crescentic glomerulonephritis; interleukin-8 and MCP-1 in chronic glomerular nephritis; and MCP-1 in lupus nephritis. It is suggested that the chemokines concern formation of pathological conditions of the above-mentioned diseases.

Until now, there are few reports as to a method for removing such chemokines which have various functions in body fluid. There is disclosed only a method for purifying blood with an adsorbent for removing an endotoxin and/or a cytokine caused by the endotoxin, which comprises a porous carrier having a cationic functional group on the surface (Japanese Unexamined Patent Publication No. 6-312017). However, there is described neither measurement of the cytokine nor adsorption of the cytokine in working examples thereof.

The application of the so-called anti-chemokine therapy is also considered wherein chemokine's action is inhibited by administering an antibody against the chemokine or a substance which inhibits binding of the chemokine to a receptor thereof. However, it is necessary to prepare and administer an antibody against each chemokine in order to inhibit such action by administration of the antibody or the like, because it is suggested that many kinds of chemokines abnormally appear in pathologic conditions accompanied with chronic inflammation such as the above-mentioned rheumatoid arthritis. Further, an antibody or the like to be administered must not exert bad influence upon a human body, and it is considered that development thereof requires long term and a great cost. Therefore, it is hard to say that such therapy is a suitable one.

In view of the problems of prior arts mentioned above, an object of this invention is to provide an adsorbent capable of efficiently removing substances related to malady in body fluid, especially small molecular weight proteins including β2-microglobulin or chemokines, a removing method capable of removing substances related to malady in body fluid, especially small molecular weight proteins including β2-microglobulin or chemokines by using said adsorbent, a device for body fluid purification and a system for body fluid purification.

A particular object of this invention is to provide a device for blood purification and a system for blood purification which are capable of removing efficiently and sufficiently small molecular weight proteins, typically β2-microglobulin or chemokines in blood and which are simple and safe.

DISCLOSURE OF THE INVENTION

The inventors of this invention have made a lot of work on adsorbents which can efficiently remove substances related to malady in body fluid, especially small molecular weight proteins, typically β2-microglobulin and chemokines.

As a result, the inventors have found that the use of a material wherein a compound having a log P value (P is a distribution coefficient in an octanol-water system) of 2.50 or more is immobilized on a water insoluble carrier, can efficiently remove substances related to malady in body fluid, especially small molecular weight proteins including β2-microglobulin and chemokines, and have accomplished this invention.

The applicant of this application previously made a patent application directed to an adsorbent for interleukins in which a compound having a log P value (P is a distribution coefficient in an octanol-water system) of 2.50 or more is immobilized on a water insoluble carrier (Japanese Patent Application No. 7-66565), and, thus, interleukin-8 having chemotaxis among interleukins (interleukin-8 is a chemokine belonging to CXC subfamily) is excluded from the scope of this invention.

In other words this invention provides an adsorbent for substances related to malady in body fluid, a method of removing substances related to malady in body fluid by adsorption, a device for body fluid purification and a system for body fluid purification as follows:

(1) An adsorbent for removing substances related to malady in body fluid wherein a compound having a log P value (P is a distribution coefficient in an octanol-water system) of 2.50 or more is immobilized on a water insoluble carrier.

(2) The adsorbent mentioned in (1), wherein the water insoluble carrier is a hydrophilic carrier.

(3) The adsorbent mentioned (1) or (2), wherein the water insoluble carrier has a porous structure.

(4) The adsorbent mentioned in (3), wherein the water insoluble carrier has a molecular weight of exclusion limit for globular protein of from $1 \times 10^4$ to $60 \times 10^4$.

(5) The adsorbent mentioned in any of (1) to (4), wherein the water insoluble carrier comprises a cellulose.

(6) The adsorbent mentioned in any of (1) to (5), wherein the water insoluble carrier is a spherical hydrogel wherein the weight ratio to water is from 1:9 to 3:7.

(7) The adsorbent mentioned in any of (1) to (6), wherein the compound having a log P value of 2.50 or more is a compound having a hydrocarbon moiety of 8 to 18 carbon atoms.

(8) The adsorbent mentioned in any of (1) to (7), which is used for adsorbing chemokines in body fluid.

(9) A method for removing substances related to malady in body fluid, wherein the adsorbent mentioned in any of (1) to (7) is brought into contact with body fluid.

(10) The removing method mentioned in (9), wherein a chemokine in body fluid is removed.

(11) A device for body fluid purification wherein a container having an inlet and an outlet for a fluid and a means for preventing an adsorbent from flowing out of the container is charged with an adsorbent comprising a water insoluble carrier and a compound having a log P value (P is a distribution coefficient in an octanol-water system) of 2.50 or more immobilized on the carrier.

(12) The device for body fluid purification mentioned in (11), wherein the water insoluble carrier is a hydrophilic carrier.

(13) The device for body fluid purification mentioned in (11) or (12), wherein the water insoluble carrier has a porous structure.

(14) The device for body fluid purification mentioned in (13), wherein the water insoluble carrier has a molecular weight of exclusion limit for globular protein of from $1 \times 10^4$ to $60 \times 10^4$.

(15) The device for body fluid purification mentioned in any of (11) to (14), wherein the water insoluble carrier comprises a cellulose.

(16) The device for body fluid purification mentioned in any of (11) to (15), wherein the water insoluble carrier is a spherical hydrogel wherein the weight ratio to water is from 1:9 to 3:7.

(17) The device for body fluid purification mentioned in (16), wherein the spherical hydrogel has an average particle size of 300 to 600 μm.

(18) The device for body fluid purification mentioned in (17), wherein $70 \times 10^4$ to $2,000 \times 10^4$ spherical particles of the hydrogel are contained in the container with an aqueous solution.

(19) The device for body fluid purification mentioned in any of (11) to (18), wherein the container is sealed and at least the inside thereof is sterilized.

(20) The device for body fluid purification mentioned in any of (11) to (19), wherein the compound having a log P value of 2.50 or more is a compound having a hydrocarbon moiety of 8 to 18 carbon atoms.

(21) The device for body fluid purification mentioned in any of (18) to (20), wherein pH, of the aqueous solution in the container is between 5 to 8.

(22) The device for body fluid purification mentioned in any of (18) to (21), wherein the aqueous solution in the container is an aqueous solution of a compound having buffer action for pH.

(23) The device for body fluid purification mentioned in any of (18) to (22), wherein the aqueous solution in the container is a solution containing citric acid and sodium citrate.

(24) The device for body fluid purification mentioned in (11), wherein a part or the whole of the container having an inlet and an outlet comprises a shaped article of a transparent resin.

(25) The device for body fluid purification mentioned in any of (11) to (24), wherein the body fluid is blood.

(26) The device for body fluid purification mentioned in any of (11) to (24), which is used for removing chemokines in body fluid.

(27) The device for body fluid purification mentioned in any of (11) to (24), which is used for removing β2-microglobulin in body fluid.

(28) A system for body fluid purification wherein the device for body fluid purification mentioned in any of (11) to (27) is connected to a dialyzer.

(29) The system for body fluid purification mentioned in (28), wherein the device for body fluid purification and the dialyzer are connected to each other in series.

Figure 1:
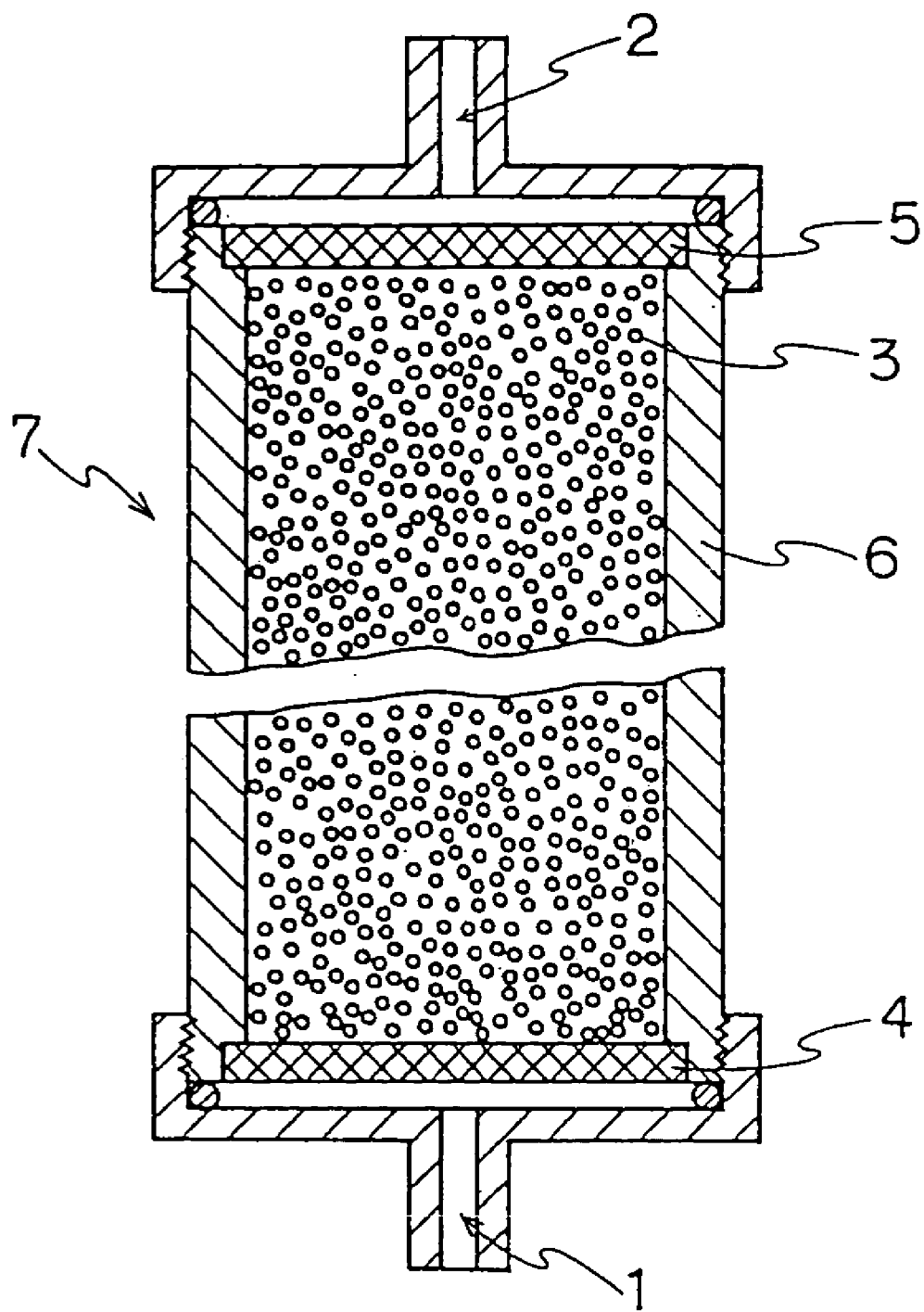
FIG. 1 is a schematic cross section showing an example of a device for body fluid purification in accordance with this invention.

The term "body fluid" in this invention means a liquid constituent derived from a living body such as blood, plasma, serum, ascites, lymph or synovia. And the term "blood" in this invention means plasma or serum wherein blood cell ingredient has been removed from whole blood as well as whole blood.

Also, the term "chemokine" in this invention means a substance which has chemotaxis and is characterized in that a gene coding for a chemokine that belongs to CXC subfamily exists in human chromosome 4 (q12-q21); and a gene coding for a chemokine that belongs to CC subfamily exists in human chromosome 17 (q11-q12). However, interleukin-8 is excluded from the chemokine in this invention. Referring to Matsushima's report (Clinical Immunology, 27 [Suppl. 16], 147-154, 1995), Chihara's report (Clinical Immunology, 27, [Suppl. 16], 162-171, 1995) and the like, human chemokines known to date are exemplified as follows: GROα, GROβ, GROγ, neutrophil activating protein-2 (NAP-2), neutrophil activating protein-4 (NAP-4), epithelial-cell derived neutrophil-activating protein-78 (ENA-78), PF-4, interferon-inducible protein 10 (IP-10), granulocyte chemotactic protein-2 (GCP-2), β-thromboglobulin (β-TG) and pre-B cell growth stimulating factor (PBSF) are exemplified as chemokines belonging to CXC subfamily, and MCP-1, HC14, monocyte chemoattractant protein-3 (MCP-3), I-309, MIP-1α, MIP-1β and RANTES are exemplified as chemokines belonging to CC subfamily.

However, since a name of a chemokine is not often unified, there is a case where one chemokine is referred to as a different name. For example, in a published book edited by Department of Microbiology, Kyoto Prefectural University of Medicine, "Cytokine Data Manual", Nankodo, 1995, there is described that GROβ and GROγ are referred to as macrophage inflammatory protein-2α (MIP-2α) and macrophage inflammatory protein-2β (MIP-2β), respectively; and MCP-1 is also referred to as monocyte chemotactic and activating factor (MCAF); and HC14 is also referred to as monocyte chemoattractant protein-2 (MCP-2). Therefore, even if the above-mentioned chemokines are referred to as another names, it is natural that such chemokines are included in the chemokine intended in this invention. Further, it is needless to say that the chemokine intended in the present invention includes a substance which will be newly found in the future and recognized to fall under the category of the definition of the chemokine.

The adsorbent of this invention for substances related to malady in body fluid, in particular, for small molecular weight proteins such as β2-microglobulin and chemokines is characterized in that a compound having a log P value of 2.50 or more is immobilized on a water insoluble carrier.

The log P value is a parameter which indicates the hydrophobicity of a compound, and a typical method of determining the distribution coefficient, P, in an octanol-water system is as follows: At first, a compound is dissolved in octanol (or water) and an equal volume of water (or octanol) is added thereto. After shaking for 30 minutes with Griffin flask shaker (made by Griffin & George Ltd.), the resultant is centrifuged for from 1 to 2 hours at 2,000 rpm. Then the respective concentrations of the compound in both octanol and water layers are measured by various methods such as spectroscopic method and GLC, and the value P is obtained according to the following formula:

$$P = C_{oct}/C_w$$

$C_{oct}$: the concentration of a compound in the octanol layer $C_w$: the concentration of a compound in the water layer Until now, many investigators have determined log P values of various compounds and the found values are put in order by C. Hansch et al (refer to "PARTITION COEFFICIENTS AND THEIR USES"; Chemical Reviews, 71, page 525 (1971)).

As to the compounds whose found values are unknown, the calculated values ($\Sigma f$) obtained by using a hydrophobic fragmental constant f, shown in R. F. Rekker's book ("THE HYDROPHOBIC FRAGMENTAL CONSTANT", Elsevier Sci. Pub. Com., Amsterdam, 1977) can be a good guide. It has been reported that hydrophobic fragmental constants f indicate the hydrophobicity of various fragments, which are determined by a statistical treatment of many found values of log P, and the sum of respective f values of the fragments which constitute a compound almost corresponds to log P of the compound. In this invention, log P value of a compound means $\Sigma f$ value when log P value of the compound is not known.

In this invention, log P value of a compound means $\Sigma f$ value when log P value of the compound is not known.

In discovering compounds effective for adsorbing substances related to malady in body fluid, in particular, for adsorbing β2-microglobulin or chemokines, compounds having various log P values have been examined in a state of being immobilized. As a result, it has been found that a compound having a log P value of 2.50 or more, preferably 2.70 or more, more preferably 2.90 or more is effective for adsorbing β2-microglobulin or chemokines and that a compound having a log P value of less than 2.5 hardly show an adsorbing ability for β2-microglobulin or chemokines. For example, in the case of immobilizing an alkylamine, it has been found that an absorbing ability for β2-microglobulin or chemokines is enhanced to a great extent when the alkylamine is changed from n-hexylamine (log P=2.06) to n-octylamine (log P=2.90).

From these results, it is guessed that the adsorption of β2-microglobulin or chemokines to the adsorbent of this invention is due to a hydrophobic interaction between β2-microglobulin or chemokines and an atomic group introduced on a carrier by immobilizing a compound having a log p value of 2.50 or more, and that a compound having a log P value of less than 2.5 cannot show an absorbing ability for β2-microglobulin or chemokines because the hydrophobicity of this compound is too low.

Moreover, it is found that the absorbing ability for β2-microglobulin or chemokines is further enhanced by replacing n-octylamine with hexadecylamine (cetylamine) ($\Sigma f=7.22$) which has a much longer alkyl chain and is more hydrophobic.

These results reveal that the adsorption of β2-microglobulin or chemokines to the adsorbent of this invention is achieved by immobilizing of a compound having a log P value of 2.50 or more and a compound having a larger log P value is preferable. For example, it is guessed that the immobilization of a compound such as octadecylamine ($\Sigma f=8.28$), which has a longer chain and is presumed to be more hydrophobic than hexadecylamine, show an adsorbing ability for β2-microglobulin or chemokines equivalent to or better than that of hexadecylamine.

The upper limit of log P value is not particularly limited, but it may be about 15 from the viewpoint of practical application.

In this invention, a compound to be immobilized onto a water-insoluble carrier can be employed without particular limitation, provided that the compound has a log P value of 2.50 or more. However, a part of a compound is often eliminated in case of binding the compound onto a carrier by chemical bonding method. In such cases, when an eliminated group greatly contributes to hydrophobicity of the compound, that is to say, when hydrophobicity of atomic group which is immobilized onto the carrier becomes smaller than $\Sigma f=2.50$ due to elimination, such compound is not suitable as the compound used in this invention from the viewpoint of the gist of this invention.

One typical example of such cases is a case when isopentyl benzoate ($\Sigma f=4.15$) is immobilized onto a carrier having hydroxyl group by transesterification. In this case, the atomic group which is actually immobilized onto the carrier is $C_6H_5$—CO—, of which the $\Sigma f$ value is 1 or less. Whether such compound is suitable or not as a compound used in this invention can be judged by determining whether the log P value of a compound obtainable by substituting an eliminating part of the compound in question by hydrogen is not less than 2.50 or not.

Among compounds having a log P value of 2.50 or more, preferable are compounds having a functional group which can be utilized for binding the compound onto a carrier, such as unsaturated hydrocarbons, alcohols, amines, thiols, carboxylic acids and derivatives thereof, halides, aldehydes, isocyanates, compounds containing an oxirane ring such as glycidyl ethers, and silyl halides. And, preferable as these compounds are compounds having a hydrocarbon moiety of 8 to 18 carbon atoms such as n-octyl group, decyl group, dodecyl group, hexadecyl group or octadecyl group.

Examples of unsaturated hydrocarbons mentioned above include 1-heptene, 1-octene, 1-decene, 1-dodecene, 1-tetradecene, 1-hexadecene, 1-octadecene, 1-eicosene, and the like.

Examples of alcohols mentioned above include n-octyl alcohol, dodecyl alcohol, hexadecyl alcohol, 1-octene-3-ol, naphthol, diphenylmethanol, 4-phenyl-butanol, and the like.

Examples of amines mentioned above include n-octylamine, decylamine, dodecylamine, hexadecylamine, octadecylamine, naphthylamine, 2-aminooctene, diphenylmethylamine, and the like.

Examples of thiols mentioned above include octanethiol, decanethiol, dodecanethiol, tetradecanethiol, hexadecanethiol, octadecanethiol, and the like.

Examples of carboxylic acids and derivatives thereof mentioned above include n-octanoic acid, nonanoic acid, 2-nonenoic acid, decanoic acid, dodecanoic acid, stearic acid, arachidonic acid, oleic acid, diphenylacetic acid, and the like. Examples of their derivatives include acid halides, esters, amides, hydrazides, and the like of the foregoing carboxylic acids.

Examples of halides mentioned above includes octyl chloride, octyl bromide, decyl chloride, dodecyl chloride, and the like.

Examples of aldehydes mentioned above include octylaldehyde, n-caprinaldehyde, dodecylaldehyde, and the like.

Examples of isocyanates mentioned above include dodecylisocyanate, hexadecylisocyanate, octadecylisocyanate, and the like.

Examples of glycidyl ethers mentioned above include dodecyl glycidyl ether, hexadecyl glycidyl ether, octadecyl glycidyl ether, and the like.

Examples of silyl halides mentioned above include n-octyltrichlorosilane, octadecyltrichlorosilane, and the like.

It is possible to use other compounds having a log P value of 2.5 or more selected from compounds in which a substituent containing a heteroatom such as halogen, nitrogen, oxygen or sulfur, or other alkyl group is substituted for hydrogen atom contained in hydrocarbon moiety of the above-exemplified compounds. Also it is possible to use compounds having a log P value of 2.5 or more shown in the above-mentioned Review by C. Hansch, "PARTITION COEFFICIENTS AND THEIR USES", Chemical Reviews, Vol. 71, 525, 1971, in tables on pages 555 to 613. However, compounds which can be used in this invention are not limited to these compounds only.

These compounds can be used either alone or in arbitrary combinations of two or more species thereof. Further these compounds can also be used in combination with a compound having a log P value of less than 2.5.

The term "water insoluble carrier" in the adsorbent of this invention means a carrier which is solid at ordinary temperature under ordinary pressure and insoluble in water. Examples of forms of the water insoluble carrier in this invention are particle, board, fiber, hollow fiber, and the like. However, not only the form thereof but also the size thereof are not particularly limited.

Typical examples of the water insoluble carrier in the adsorbent of this invention are inorganic carriers such as glass beads and silica gel, organic carriers each comprising synthetic polymers such as cross-linked polyvinyl alcohol, cross-linked polyacrylate, cross-linked polyacrylamide and cross-linked polystyrene, or polysaccharides such as celluloses, cross-linked agarose and cross-linked dextrin, and composite carriers each obtained by a combination of the above-mentioned materials such as organic-organic carriers and organic-inorganic carriers.

Among these carriers, hydrophilic carriers are preferable since non-specific adsorption is comparatively a little and adsorption selectivity for β2-microglobulin or chemokines is good. Herein, the term "hydrophilic carrier" refers to a carrier composed of a material which has a contact angle with water of 60 degrees or less when the material is shaped into a flat plate.

Various measuring methods for contact angle with water are known. But a method wherein a drop of water is placed on a flat plate of a material to be measured, is the most common method, for example, as shown in Ideka's bood, "Selected Books on Experimental Chemistry-Colloid Chemistry", Chapter 4, "Thermodynamics of Interface", Syokabo, pages 75-104, 1986.

Typical examples of carriers of which the contact angle with water is 60 degrees or less as measured by the method mentioned above, are those comprising celluloses, polyvinyl alcohol, hydrolyzed ethylene-vinyl acetate copolymer, polyacrylamide, polyacrylic acid, polymethacrylic acid, polymethyl methacrylate, polyacrylic acid-grafting polyethylene, polyacrylamide-grafting polyethylene, glass, and the like.

Further it is shown in a book that the contact angle of the above-mentioned cellulose with water is about 18 degrees (see Yoshito Ikada, "Medical Polymer Materials", Kyoritu Pub., page 65, 1989).

It is more preferable that these water insoluble carriers have a lot of fine pores of suitable size, that is, has a porous structure.

The term "carrier having a porous structure" includes the followings: a carrier comprising globular particles each formed by agglomeration of microglubular particles of a macromolecular material and which has spaces (macropores) formed between the agglomerated microglobular particles; a carrier comprising the globular particles wherein each microglobular particle contains pores; and a carrier comprising a copolymer having a three-dimensional network structure (polymer network) which contains pores (micropores) formed in a swollen state in an organic solvent having affinity with the copolymer.

Further from the viewpoint of the adsorption capacity per unit volume of an adsorbent, a carrier which is porous throughout the whole thereof preferable to a carrier of which only the surface is porous, as the water insoluble carrier of a porous structure, and the pore volume and the specific surface area are preferably as large as possible so long as the adsorbing ability is not hindered.

As a carrier which satisfies these desirable requirements, a porous gel of a cellulose is given.

Porous cellulose gel is one of the most suitable carriers since it has the following superior properties: (1) The gel is hardly destroyed or becomes fine powder by an operation such as an agitation because it has a comparatively high mechanical strength and toughness, and when a column is charged with the gel, it is possible to flow a body fluid with a high flow rate because the gel is not compacted even if the body fluid is flowed at a high flow rate, and further the porous structure of the gel is hard to receive a change by a high pressure steam sterilization. (2) The gel is hydrophilic since the gel is composed of a cellulose, and there are many hydroxyl groups which can be used for bonding ligand, and non-specific adsorption hardly occurs. (3) An adsorption capacity which is comparable to soft gel can be obtained even when the pore volume is made large because the gel has a comparatively high strength. (4) The gel is safer than synthetic polymers and the like.

The term "cellulose" in this invention refers to at least one of natural celluloses, regenerated celluloses and cellulose derivatives. Examples of natural celluloses are cotton fibers from which fat is removed, fibers of hemps, pulps obtained by removing lignin or hemi-cellulose from wood, and refined celluloses which are obtained by refining the pulps.

The term "regenerated cellulose" means a cellulose which is obtained by transforming a natural cellulose into a cellulose derivative and then regenerating the cellulose derivative by hydrolysis or the like. Cellulose derivatives, for example, include those obtained by esterifying and/or etherealizing a part or the whole of hydroxyl groups of a natural or regenerated cellulose.

Typical examples of the cellulose derivative obtained by esterifying a part or the whole of hydroxyl groups of a cellulose are cellulose acetate, cellulose propionate, cellulose butyrate, nitrocellulose, cellulose sulfate, cellulose phosphate, cellulose acetate butyrate, cellulose nitrate and esters of cellulose with dicarboxylic acid. However, cellulose esters are not limited to these examples.

Typical examples of the cellulose derivative obtained by etherealizing a part or the whole of hydroxyl groups of a cellulose are methyl cellulose, ethyl cellulose, benzyl cellulose, cyanoethyl cellulose, carboxymethyl cellulose, aminoethyl cellulose and hydroxyethyl cellulose. However, etherealized celluloses are not limited to these examples.

In this invention, the above-mentioned carriers can be used either alone or in an arbitrary combination of two or more species thereof.

The water insoluble carrier having such porous structure preferably has a characteristic that a substance being an object for adsorption can enter fine pores thereof at some large probability but other proteins enter the pores as little as possible.

In other words, the molecular weight of β2-microglobulin is about 11,700 and chemokines often exist as a protein having a molecular weight of about 6,000-10,000, both of which are objects to be adsorbed with the adsorbent of this invention. Thus it is preferable that β2-microglobulin or chemokines can enter the fine pores at some large probability but other proteins enter the pores as little as possible in order to adsorb β2-microglobulin or chemokines effectively.

As a measure of the molecular weight of a substance which can enter a fine pore, a molecular weight of exclusion limit is generally used. The term "molecular weight of exclusion limit" means the minimum molecular weight of a molecule among molecules which cannot enter a fine pore (i.e. excluded) in a gel permeation chromatography as described in books (see, for example, Hiroyuki Hatano and Toshihiko Hanai, "Experimental High Performance Liquid Chromatography", Kagaku Dojin).

The molecular weight of exclusion limit is generally well examined with use of globular protein, dextran, polyethylene glycol or the like. In the case of the carrier used in this invention, it is preferable to use the value obtained by using globular protein.

As a result of study using carriers of various molecular weights of exclusion limit, it has become clear that the range of molecular weight of exclusion limit for globular protein which is suitable for adsorbing β2-microglobulin or chemokines is from $1 \times 10^4$ to $60 \times 10^4$.

That is, the amount of β2-microglobulin or chemokines adsorbed is small when a carrier having a value of less than $1 \times 10^4$ as a molecular weight of exclusion limit for globular protein is used and the practicability thereof becomes low. The amount of adsorbed proteins (mainly albumin) other than β2-microglobulin and chemokines becomes large when a carrier having a value of more than $60 \times 10^4$ as a molecular weight of exclusion limit is used and the practicability thereof becomes low from the viewpoint of selectivity.

Accordingly, the range of molecular weight of exclusion limit for globular protein of the carrier used in this invention is preferably from $1 \times 10^4$ to $60 \times 10^4$, more preferably from $2 \times 10^4$ to $50 \times 10^4$, and specially preferably from $3 \times 10^4$ to $40 \times 10^4$.

Further it is preferable that the carrier has functional groups which can be used in an immobilizing reaction for a ligand. Typical examples of the functional group are hydroxyl group, amino group, aldehyde group, caroxylic group, thiol group, silanol group, amide group, epoxy group, halogen group, succinimide group, acid anhydride group, trecyl group, and the like. However, the functional groups used in this invention are not limited to those.

Any one of a hard carrier and a soft carrier can be used as a carrier in this invention. In the case of using an adsorbent for an extracorporeal circulation, it is important that the adsorbent does not clog up when it is charged in a column and a fluid is flowed through the column. In such a case enough mechanical strength is demanded for the adsorbent. Accordingly it is more preferable to use a hard carrier in this invention.

Herein the term "hard carrier" refers to e.g. in the case of a granulated gel, a gel which has such a property that there is a linear relation between pressure drop ΔP and flow rate up to a pressure drop of 0.3 kg/cm² when the gel is uniformly charged in a cylindrical column and an aqueous fluid is flowed through it, as shown in Reference Example mentioned below.

The adsorbent of this invention is obtained by immobilizing a compound having a log P value of 2.50 or more on a water insoluble carrier, and various kinds of conventional methods can be used as the immobilizing method without particular limit.

However, when the adsorbent of this invention is used for an extracorporeal circulation treatment, it is important to suppress the elimination or elution of a ligand as much as possible in sterilization or treatment from the viewpoint of safety. Thus immobilization by a covalent bond method is preferable.

In the adsorbent of this invention, it is preferable that a proper amount of a compound having a log P value of 2.50 or more is immobilized. When the amount of the compound immobilized is too small, β2-microglobulin or chemokines are not adsorbed. When the amount is too much, platelets are prone to adhere to the adsorbent in the case that blood is used as body fluid.

Thus, the amount of a compound having a log P value of 2.50 or more to be immobilized is from 10 to 1,000 μmol per 1 g of a dry weight of a water insoluble carrier, and more preferably from 50 to 500 μmol, and most preferably from 100 to 300 μmol.

As the adsorbent of this invention, a hydrogel having a colloidal solid phase which comprises a cellulose on which a compound having a log P value of 2.50 or more is immobilized (hereinafter referred to as C-cellulose) and water is preferable, and further it is preferable that a weight ratio of C-cellulose and water is in a range of 1:9 to 3:7. This adsorbent is explained in detail as follows:

As a method for immobilizing a compound having a log P value of 2.50 or more on a cellulose, various conventional methods such as a physical binding method, a binding method through an ionic bond and a binding method through a covalent bond, etc. can be used, but a binding method through a covalent bond is the most preferable because it is important that an immobilized compound is hard to be eliminated.

Examples of concrete means include a method of directly bonding the compound to a cellulose through ester bond, amide bond, ether bond, thioether bond, urethane bond or the like by utilizing hydroxyl groups of the cellulose and a method of bonding the compound to a cellulose after enhancing the reactivity of the cellulose (activating) by introducing functional group such as amino group, aldehyde group, epoxy group or carboxyl group into the cellulose. And, as a concrete method of activating a cellulose by introducing functional group thereinto, a bromocyanogen method, an epoxidating method, a trecyl chloride method and a periodate oxidation method are given, but the method is not limited to only these examples.

As described above, the term "hydrogel" in this invention means a colloidal solid phase containing water or an aqueous solution as an essential ingredient, and a gel skeleton, that is, a xerogel which remains after removing the water from the hydrogel by drying is outside the concept of "hydrogel" intended in this invention.

The weight ratio of C-cellulose and water in the hydrogel is determined by using the weight of a hydrogel (wet weight: Ww) obtained after removing an adsorbed water and an interstitial water between hydrogel particles by filtration with suction or centrifugation and the weight of the hydrogel (dry weight: Wd) obtained after the weight becomes constant by drying the hydrogel. Thus, the ratio of Wd: (Ww-Wd) is a weight ratio of C-cellulose and water in this invention.

As a concrete method of obtaining the wet weight, a method is given wherein the weight of a hydrogel is measured after an elapse of a sucking time required till, the slope of a weight reducing curve becomes small. Herein the weight reducing curve is obtained from a relation between a sucking time and a weight when a hydrogel taken on a glass filter is sucked by using an aspirator.

And the drying method is not particularly limited so long as a constant weight can be obtained, but a method of drying at about 105° C. under an ordinary pressure can be simply used because a special device is not required.

The range of weight ratio of C-cellulose and water which constitute the hydrogel of this invention is from 1:9 to 3:7. This ratio is based on the following: A C-cellulose ratio of not less than 1/9 is preferable from the viewpoint of preventing deformation of a hydrogel due to pressure drop and a compaction accompanying the deformation in a case where body fluid is passed through a device for body fluid purification. A C-cellulose ratio of not more than 3/7 is preferable from the viewpoint of preventing a decreasee in adsorbing rate.

Preferably the shape of hydrogel particles contained in a device for body fluid purification in accordance with this invention, especially the shape of hydrogel particles contained in a device for blood purification is spherical. Herein the term "spherical" means not only to be truly spherical but also to be spheroidal.

With respect to the hydrogel of this type, particles having an average size of not more than 300 μm are generally used due to a high adsorbing rate in a case of treating body fluid which does not almost contain a cellular ingredient, such as plasma, while particles having an average size of 250 to 1,000 μm are preferably used in a case of a direct hemoperfusion system in order to keep a sufficient flow path for blood corpuscles.

With respect to spherical hydrogel particles of this invention, especially spherical hydrogel particles which is contained in a device for blood purification, the average particle size is preferably from 300 to 600 μm from the viewpoint of compatibility between flowability of blood corpuscle ingredient and adsorbing rate.

Spherical hydrogel particles comprising a cellulose and having an average particle size of 430 to 600 μm and, more particularly, 430 to 500 μm, provide a significantly higher passing ratio for leukocytes and erythrocytes as well as platelets passing through a column packed with the particles and produce an insignificant change in pressure difference during the passing of blood through the column as compared to smaller particles.

Herein the term "average particle size" refers to a number average particle size. The average particle size is obtained, for example, by averaging particle sizes of 20 to 50 hydrogel particles, which are measured with magnification of about 10 to about 50 by using a stereoscopic microscope.

When hydrogel particles are spheroidal, a longer axis is assumed to be a particle size and an average size is determined by using the same method as mentioned above.

Particles having a particle size within the range mentioned above can be used without special limit as to particle size distribution. However, particles of a narrow particle size distribution, which can be produced, for example, by forming uniform liquid drops by the vibration method described in Japanese Unexamined Patent Publication No. 63-117039 and solidifying the drops under a proper condition, are preferable, especially when they are used in a direct hemoperfusion system.

As a method of producing hydrogel particles comprising a C-cellulose in accordance with this invention, any one of a method of producing hydrogel particles by transforming a cellulose into a C-cellulose and then forming the C-cellulose into particles, and a method of producing hydrogel particles from a cellulose and then immobilizing a compound having a log P value of 2.50 or more on the hydrogel particles is usable.

Concrete examples of the method of producing hydrogel particles by transforming a cellulose into a C-cellulose and then shaping the C-cellulose into particles include: a method wherein a C-cellulose is produced by immobilizing a compound having a log P value of 2.50 or more to a cellulose, and the C-cellulose is dissolved into a solvent to give a solution, and the solution is formed into drops which are coagulated to give hydrogel particles; and a method wherein, in the case that there is no suitable solvent to prepare a solution of the C-cellulose, the C-cellulose is converted into a derivative, which is easily soluble in a solvent, by esterification or etherealization, and hydrogel particles are prepared from the derivative; and like method. But the method is not limited to these examples.

In the method of producing hydrogel particles of a cellulose and immobilizing a compound having a log P value of 2.50 or more, a method comprising dissolving a cellulose into a solvent, forming drops of the solution and solidifying the drops is given as a method of producing cellulose hydrogel particles. In such a case, a method of using a cellulose derivative as a cellulose is preferably used because there are various solvents to be used and thus the selection range of production conditions becomes broad. Cellulose derivatives to be used include those obtained by esterifying and/or etherealizing a part or the whole of hydroxyl groups of a cellulose which are mentioned above. Among them, cellulose esters such as cellulose acetate and cellulose propionate are preferably used because they can be dissolved into various kinds of solvents. Such a cellulose derivative is transformed into hydrogel particles, and a compound having a log P value of 2.50 or more is immobilized onto the hydrogel particles as they are, or after hydrolyzing if necessary, thereby giving hydrogel particles of C-cellulose.

There are various kinds of methods for removing substances related to malady, especially β2-microglobulin or chemokines from body fluid by using the adsorbent of this invention.

The most simple method is a method wherein body fluid is taken out and stored in a bag or the like and the adsorbent is mixed therewith to allow to adsorb substances related to malady and then the adsorbent is filtered off to obtain the body fluid from which the substances are removed.

Another method is a method wherein a container having an inlet and an outlet for body fluid and which is equipped at the outlet with a filter through which body fluid can pass and the adsorbent cannot pass is charged with the adsorbent, and body fluid is flowed through the container.

Either method can be used. With respect to the latter method, however, the operation thereof is simple, and substances related to malady can be removed efficiently on-line from body fluid, especially blood of a patient by incorporating the latter method in an extracorporeal circulation circuit. Thus, the adsorbent of this invention is suitable for the later method.

Next, by referring to FIG. 1, an example of a device for body fluid purification for removing substances related to malady using the above-mentioned adsorbent in accordance with this invention will be explained.

In FIG. 1, 1 denotes an inlet for body fluid, 2 denotes an outlet for body fluid, 3 denotes the adsorbent of this invention, 4 and 5 denote a filter through which body fluid and ingredients contained in body fluid can pass but the adsorbent cannot pass, 6 denotes a column and 7 denotes a device for body fluid purification.

However, the device for body fluid purification in accordance with this invention is not limited to such an example, and any device having various structures can be used so long as the device has a structure wherein a container having an inlet and an outlet for fluid and equipped with a means for preventing an adsorbent from flowing out of the container is charged with the adsorbent mentioned before.

As examples of the means for preventing the adsorbent from flowing out, filters such as mesh, nonwoven fabric and cotton stopper, etc. are given.

And there is no particular limitation as to the shape, material and size of the container, but a preferable typical example of the container is a transparent or semitransparent cylindrical container having a capacity of about 150 to 500 ml and a diameter of about 4 to 10 cm. Particularly preferable materials are those having a sterilization-resistance. Typical examples are, for instance, glass coated with silicone, polypropylene, polyvinyl chloride, polycarbonate, polysulfone and polymethylpentene.

Next, as a preferable embodiment of the device for body fluid purification in accordance with this invention, a device for blood purification using the hydrogel of C-cellulose as adsorbent will be explained. It is needless to say that the construction of this device for blood purification can be generally applied to body fluids other than blood.

A device for blood purification in accordance with this invention comprises a container charged with a hydrogel of a C-cellulose wherein the container has an inlet and an outlet for blood and is equipped at least at the outlet with a means for preventing the hydrogel from flowing out, through which blood can pass but the hydrogel cannot pass.

As the means for preventing the hydrogel from flowing out, filters such as mesh, nonwoven fabric and cotton stopper, etc. are given, and polypropylene, polyethylene, polyester, etc. can be used as the material thereof.

And there is no particular limitation as to the shape, material and size of the container, but a preferable typical example of the container is a transparent or semitransparent cylindrical container having a capacity of about 150 to 500 ml and a diameter of about 4 to 10 cm. Preferable materials are those having a sterilization-resistance. Typical examples are, for instance, glass coated with silicone, polypropylene, polycarbonate, polysulfone, polymethylpentene and polyvinyl chloride. Polypropylene and polycarbonate are preferable due to their good moldability, strength and chemical resistance, and, further, polycarbonate is particularly preferably used because it has a high transparency and thus it, is possible to confirm an abnormality in the device for blood purification by visual inspection before use, during use and after use.

The number of hydrogel particles contained in the device for blood purification in accordance with this invention can be obtained by converting the number of hydrogel particles per unit volume to that per volume of the device for blood purification. When the number of hydrogel particles is less than $70 \times 10^4$, enough adsorbing capacity can not be obtained. When more than $2000 \times 10^4$ particles are contained, the volume of a device for blood purification becomes large as exceeding 500 ml and there is no practicability because the amount of blood for an extracorporeal circulation becomes quite large and a load of a patient also becomes heavy.

There is particularly no limit to the ratio of the volume of hydrogel contained in the container to the volume of the space for containing hydrogel in the container. For example, a volume of unnecessary blood volume increase for an extracorporeal circulation does not result.

Figure 2:
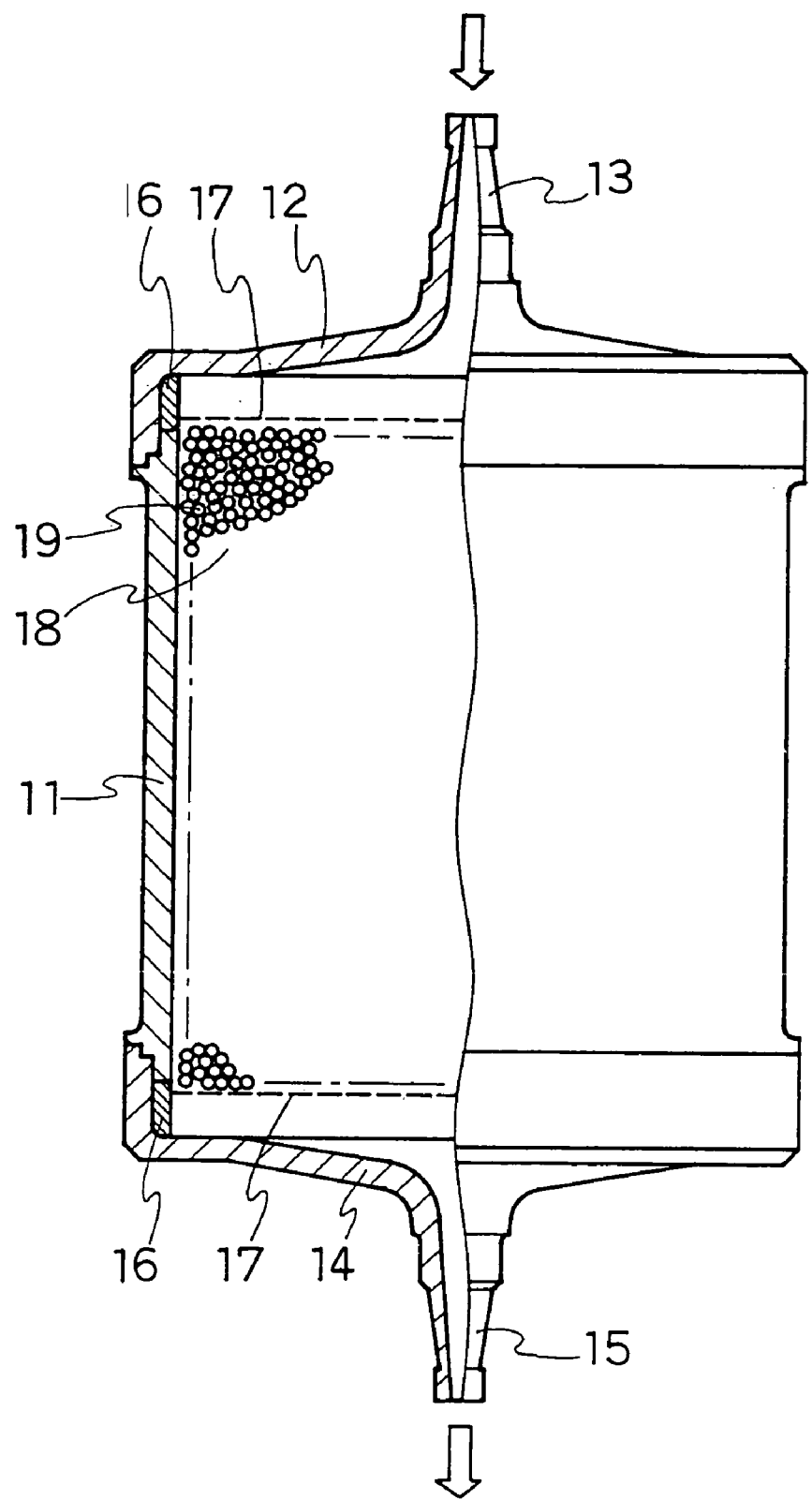
FIG. 2 is a side elevation view, partly in cross section, showing an example of a device for blood purification in accordance with this invention.

An example of the device for blood purification in accordance with this invention is shown in FIG. 2. However, the device for blood purification in accordance with this invention is not limited to such an example.

In FIG. 2, 11 denotes a cylindrical container body, and the upper opening and lower opening of the container body 11 are liquid-sealed with an upper lid 12 and a lower lid 14, respectively. The upper lid 12 is equipped with an inlet nozzle 13 for blood and the lower lid 14 is equipped with an outlet nozzle 15 for blood 17 denotes mesh mounted to a mesh frame 16. The mesh on blood inlet side can be omitted.

18 denotes an aqueous solution (filling liquid) and 19 denotes spherical hydrogel particles.

An aqueous solution contained in the device for blood purification of this invention with hydrogel of a C-cellulose, that is, filling liquid, can be fundamentally any kind of aqueous solution so long as it does not give any bad effect on a human body, but the pH value of the filling liquid is preferably in the range of 5 to 8 in order to prevent the hydrogel from being damaged in a sterilization operation.

And in the case that there is a possibility that change of pH in the device for blood purification may occur due to a change of temperature in a sterilization operation, it becomes possible to keep the pH change width of filling solution small by using an aqueous solution of a compound having a buffer effect for pH change. Thus a buffer solution is preferably used as a filling solution.

Preferable typical examples of compounds mentioned above are compounds which are safe for human body, inclusive of phosphoric acid, acetic acid maleic acid, citric acid, boric-acid, tartaric-acid, glycine, etc., and sodium salts, potassium salts and calcium salts of these compounds. These compounds may be used either alone or in combination of two or more species thereof.

Further, an aqueous solution of citric acid and its sodium salt as compounds mentioned above is preferably used because it has actual results as a filling liquid in commercially available devices for blood purification for use in plasma perfusion.

As typical examples of a sterilization method for the device for blood purification of this invention, a high pressure steam sterilization, γ-ray sterilization and a sterilization using a water-soluble agent are given. And any method can be used without any particular limitation so long as it can cause death of bacteria in the presence of water. A high pressure steam sterilization is preferably used because it does not give a severe damage to the hydrogel and any harmful agent does not remain since no special agent is used.

The device for body fluid purification in accordance with this invention can be used not only singly in the above-mentioned extracorporeal circulation circuit but also in a combination with other extracorporeal circulation therapy system. As examples of such combination, there are a combination with an artificial dialysis circuit, and the like, and the device can be used in a combination with dialysis therapy.

The device for blood purification of this invention wherein hydrogel of a C-cellulose is used as an adsorbent can be used either in a method of perfusing plasma or in direct hemoperfusion, as mentioned above.

Further the device for blood purification of this invention can be used alone in a blood circuit wherein only the device of this invention is incorporated, or the device of this invention can be used in combination with other device for blood purification such as hemodialyzer or blood adsorbing device.

When the device for blood purification of this invention is used in combination of a hemodialyzer, either a series connection or a parallel connection can be used, but the series connection is preferably used because it does not result in complications of blood circuit or troublesome operation.

By using a system for blood purification wherein the device for blood purification of this invention and a hemodialyzer are connected in series, it is possible to remove small molecular weight proteins including β2-microglobulin and chemokines, which cannot be removed sufficiently by hemodialysis alone. And also the system is easy in operation and is a simple system which does not need an additional fluid replacement. Thus this system is suitable for purifying blood of a renal insufficient patient.

Further in the case of the series connection, either the device for blood purification of this invention or hemodialyzer can be provided at an upper stream side.

Figure 3:
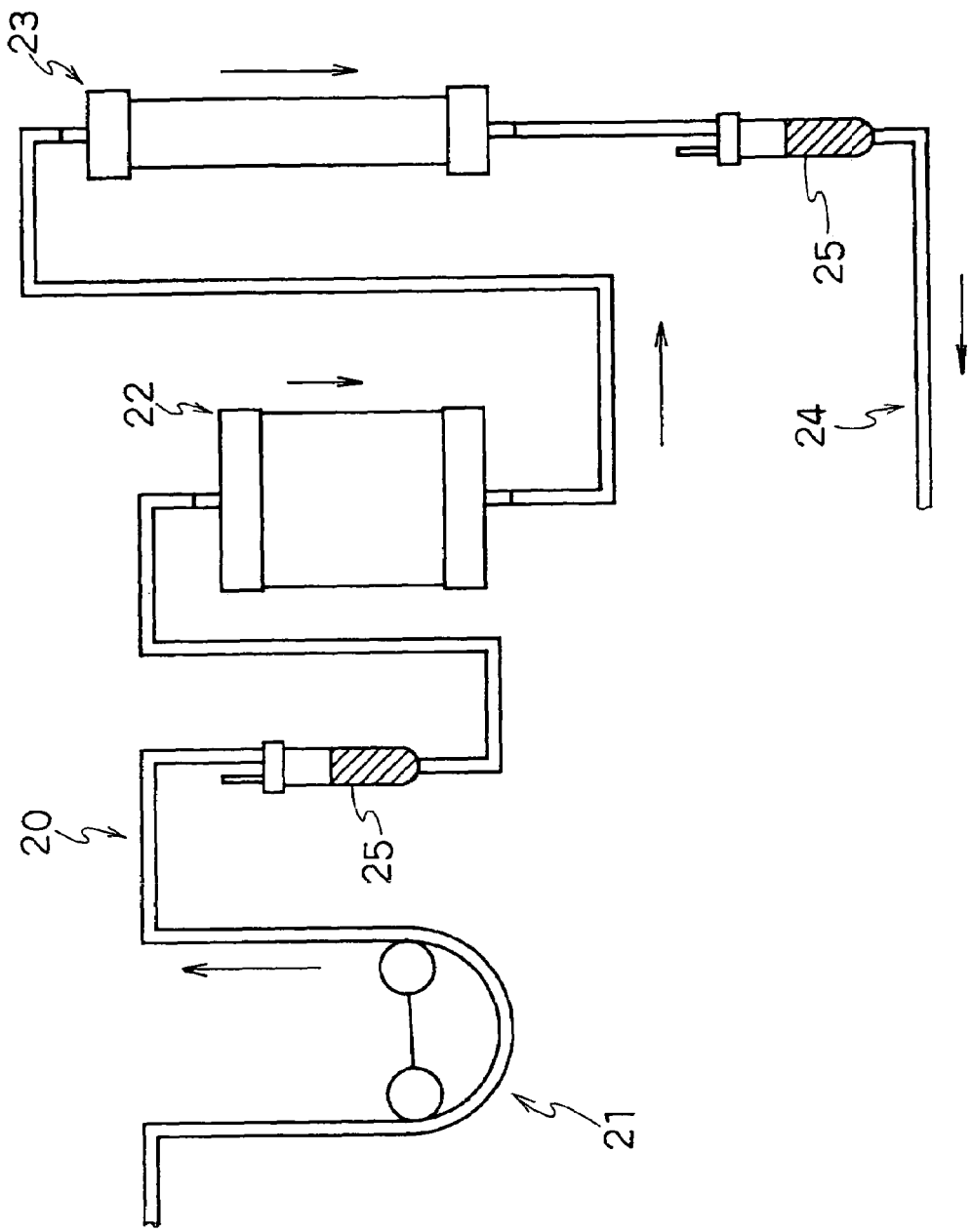
FIG. 3 is a schematic illustration showing an example of a system for blood purification in accordance with this invention.
Figure 4:
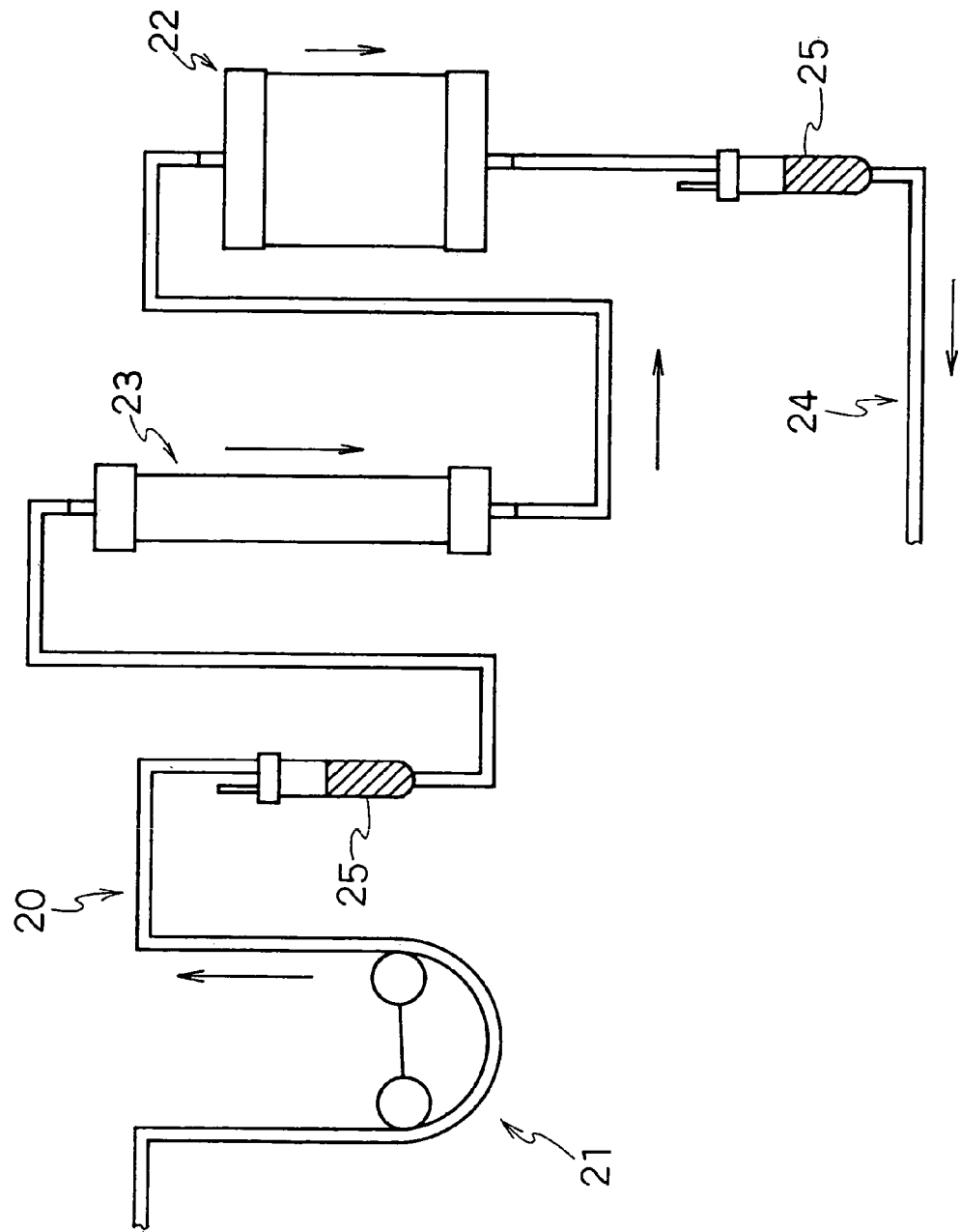
FIG. 4 is a schematic illustration showing another example of a system for blood purification in accordance with this invention.

An example of the system for blood purification in accordance with this invention is shown in FIG. 3 and another example in FIG. 4.

In FIG. 3, 20 denotes an arterial circuit including a blood pump 21, and a device for blood purification 22 of this invention and a hemodialyzer 23 are connected in series in this order in the down stream of the arterial circuit 20. The hemodialyzer 23 is connected to a venous circuit 24. 25 denotes a dripping chamber. In FIG. 3 arrows indicate a blood flow direction.

In another example of the system for blood purification shown in FIG. 4, the hemodialyzer 23 and the device for blood purification 22 are connected in series in this order in the down stream of the arterial circuit 20.

BEST MODE FOR CARRYING OUT THE INVENTION

In the following, this invention is explained in detail by referring to Examples, but this invention is not limited to these Examples.

REFERENCE EXAMPLE

Each of cylindrical glass columns (inner diameter: 9 mm, length of column: 150 mm) equipped with filters having a pore size 15 μm at both ends, was charged uniformly with an agarose gel (Biogel A-5m made by Bio-rad Laboratories, particle size: 50 to 100 meshes), a vinyl polymer gel (TOYOPEARL HW-65 made by TOSOH Corporation, particle size: 50 to 100 μm) or a cellulose gel (CELLULOFINE GC-700m made by Chisso Corporation, particle size: 45 to 105 μm). The relationship between flow rate and pressure drop ΔP was determined by passing water through the column with a peristatic pump. The results are shown in FIG. 5.

Figure 5:
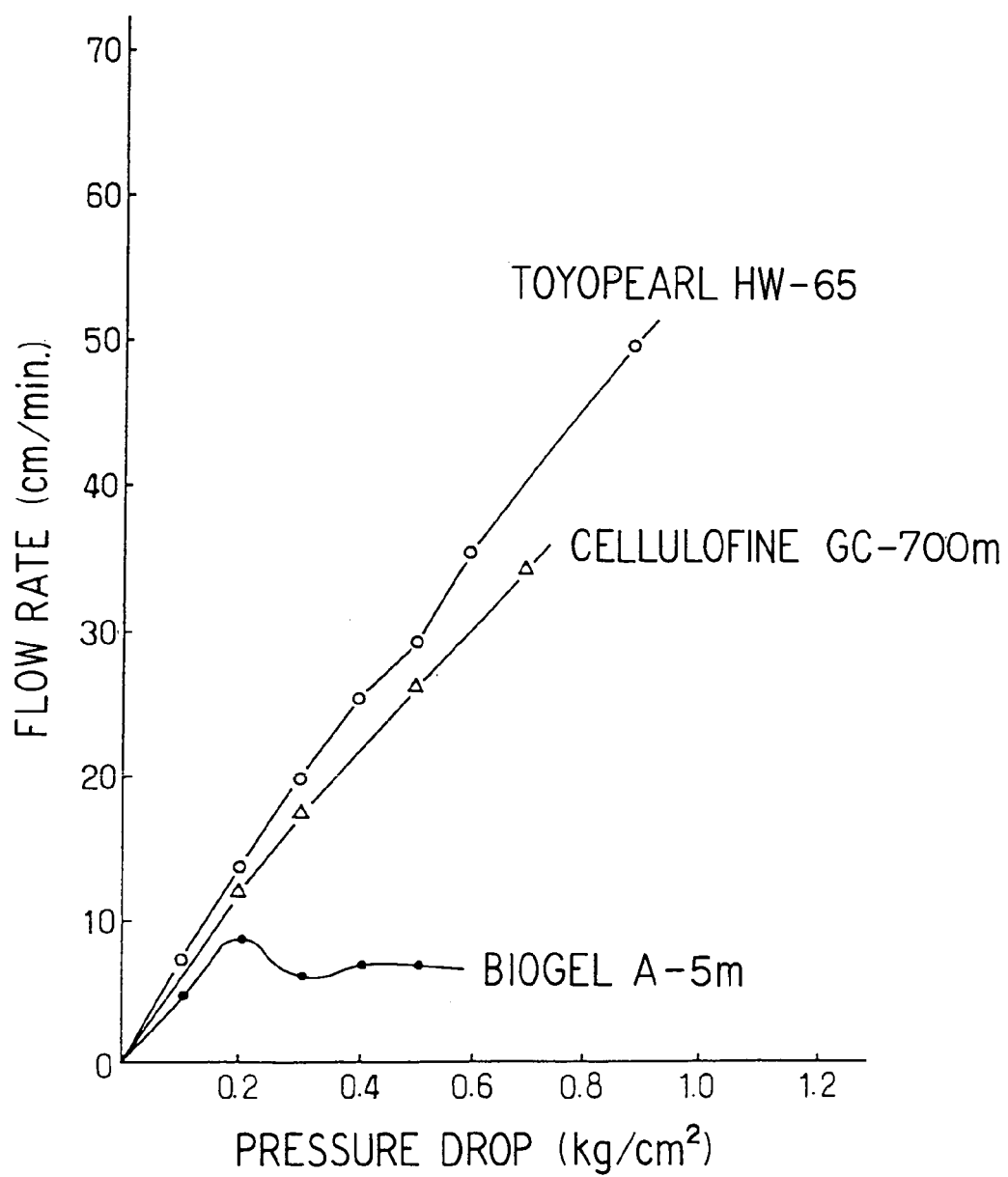
FIG. 5 is a graph showing a relation between the flow rate and pressure drop in a column charged with a gel.

As shown in FIG. 5, it is found that each flow rate in cases of TOYOPEARL HW-65 and CELLULOFINE GC-700m increases almost in proportion to an increase in pressure, while Biogel A-5m causes a compaction and the flow rate does not increase even if the pressure is increased.

In this invention, the gel showing the characteristics that pressure drop and flow rate are in linear relationship up to a pressure drop of 0.3 kg/cm$^2$ as the former, refers to hard gel.

Examples of 1-3 are related to removal of β2-microglobulin in purification of blood of renal insufficient patient.

EXAMPLE 1

Spherical hydrogel particles of a cellulose acetate were obtained by dissolving a commercially available cellulose acetate in a mixed solvent of dimethyl sufoxide and propylene glycol, forming the resulting solution into droplets and solidifying them by the method mentioned in Japanese Unexamined Patent Publication No. 63-117039 (vibration method).

The hydrogel particles were mixed with an aqueous solution of sodium hydroxide to undergo a hydrolysis reaction, giving hydrogel particles of a cellulose.

The hydrogel particles of a cellulose were allowed to react with epichlorohydrin in the aqueous solution of sodium hydroxide and then to react with hexadecylamine in an aqueous solution of alcohol, giving spherical hydrogel particles of a cellulose on which hexadecylamine was immobilized (average particle size: 460 μm).

In the spherical hydrogel particles of a cellulose on which hexadecylamine was immobilized (the immobilized quantity: 175 μmol/g-dry weight), the weight ratio of the cellulose on which hexadecylamine was immobilized and water was 2:8, and the number of spherical hydrogel particles included in 1 ml of sedimentation volume was 9,800 as measured by counting.

These hydrogel particles were charged into a 350 ml transparent container (material: polycarbonate) having an inlet and an outlet for blood equipped at both inlet and outlet with meshes having a pore size of 150 μm (material: polyester) (the calculated gel particle number in the container: $343 \times 10^4$), and a buffer solution containing 500 ppm of citric acid and sodium citrate adjusted to pH 6 to 6.5 was charged as filling liquid and a high pressure steam sterilization was performed at 121° C. for 20 minutes. Thus a device for blood purification was produced.

After this device for blood purification was washed with 1 liter of physiological saline and further washed with 1 liter of physiological saline containing 10 U/ml of heparin, it was connected with a hemodialyzer (Filtral 16, made by Hospal Corporation) in series as shown in FIG. 3 and an extracorporeal circulation of patient blood was performed with a blood flow rate as in a usual hemodialysis (200 ml/minute).

The concentration of β2-microglobulin in blood before and after 4-hour extracorporeal circulation was measured by RIA·2 antibody method. Blood after 4 hour circulation was taken from an upper stream of the device for blood purification shown in FIG. 2. The concentration of β2-microglobulin in blood before extracorporeal circulation was 39.4 mg/l, while it was lowed to 7.7 mg/l after 4-hour circulation.

Further, from a change of β2-microglobulin concentration with time in the upper and down stream of the device for blood purification and that of the down stream of the hemodialyzer, the removed quantity of β2-microglobulin was calculated to be 239 mg by the device for blood purification and 263 mg by the system for blood purification.

EXAMPLE 2

A device for blood purification produced and washed in the same manner as in Example 1 was connected with a hemodialyzer (Filtral 16, made by Hospal Corporation) in series as shown in FIG. 4 and an extracorporeal circulation of patient blood was performed with a blood flow rate as in a usual hemodialysis (200 ml/minute).

The concentration of β2-microglobulin in blood before and after 4-hour extracorporeal circulation was measured by RIA·2 antibody method. Blood after 4-hour circulation was taken from an upper stream of the hemodialyzer shown in FIG. 4.

The concentration of β2-microglobulin in blood before extracorporeal circulation was 32.6 mg/l, while it was lowed to 7.5 mg/l after 4-hour circulation.

Further, from a change of β2-microglobulin concentration with time in the upper stream of the hemodialyzer and that of the down stream of the device for blood purification, the removed quantity of β2-microglobulin by the system for blood purification was calculated to be 258 mg.

EXAMPLE 3

A device for blood purification produced and washed in the same manner as in Example 1 was connected with a hemodialyzer (BK-1.6 P, made by Toray Industries, Inc.) in series as shown in FIG. 3 and an extracorporeal circulation of patient blood was performed with a blood flow rate as in a usual hemodialysis (200 ml/minute).

The concentrations of β2-microglobulin, lysozyme and myoglobin in blood before and after 4-hour extracorporeal circulation were measured by RIA·2 antibody method, nephelometry and RIA·PEG method, respectively, and it was found that the concentrations of β2-microglobulin, lysozyme and myoglobin before extracorporeal circulation were 41.5 mg/l, 46.0 mg/l and 711.0 ng/ml, respectively, and those after 4-hour extracorporeal circulation were 11.5 mg/l, 17.8 mg/l and 212.5 ng/ml respectively.

Comparative Example 1

Four-hour hemodialysis was performed to the same patient shown in Example 3 (hemodialyzer: BK-1.6P made by Toray Industries, Inc.).

The concentrations of β2-microglobulin, lysozyme and myoglobin were measured by RIA·2 antibody method, nephelometry and RIA·PEG method, respectively, and it was found that the concentrations of β2-microglobulin, lysozyme and myoglobin before hemodialysis were 32.1 mg/l, 43.0 mg/l and 567.0 ng/ml, respectively and those after 4 hour-hemodialysis were 22.4 mg/l, 34.0 mg/l and 286.9 ng/ml, respectively.

From these results, it is seen that the device for blood purification and the system for blood purification in accordance with this invention are a safe and simple device for blood purification and system for blood purification which can sufficiently remove small molecular weight proteins represented by β2-microglobulin.

Next Examples 4-8 are related to removal of chemokines in human serum. In these Examples, MIP-1α, which is one of CC subfamily, was picked up as an adsorption object among chemokines, but it is needless to say that it is also possible to perform with other chemokines.

EXAMPLE 4

To 170 ml of CELLULOFINE GC-700m (molecular weight of exclusion limit for globular protein: 400,000, made by Chisso Corporation) which is a cellulose porous carrier was added water so that the total volume become 340 ml. Thereto was added 90 ml of a 2M aqueous solution of sodium hydroxide, followed by heating to 40° C. 31 ml of epichlorohydrin was added thereto and the reaction was conducted with agitating at 40° C. for two hours. After the reaction, the resultant was sufficiently washed with water to give an epoxidated carrier.

To 10 ml of this epoxidated carrier was added 200 mg of n-octylamine (log P=2.90), and the mixture was allowed to stand for reaction in a 50 (v/v) % aqueous solution of ethanol at 45° C. for six days. After the reaction, the resultant was fully washed with a 50 (v/v) % aqueous solution of ethanol, ethanol, a 50 (v/v) % aqueous solution of ethanol and water in this order, yielding n-octylamine-immobilized carrier. The immobilized quantity of n-octylamine was 184 μmol/dry weight of the carrier (1 g).

Three ml of MIP-1α added-normal human serum (the concentration of MIP-1α: 1.1 ng/ml) which was prepared by adding recombinant human MIP-1α (made by R & D Systems Corporation) to a normal human serum (made by Dainippon Pharmaceutical Co., Ltd.) was added to each of 0.5 ml of this immobilized carrier and 0.5 ml of CELLULOFINE GC-700 m, and each mixture was incubated with shaking at 37° C. for two hours.

Concentrations of MIP-1α in the supernatant before and after the incubation were measured by using a kit for measuring human MIP-1α made by R & D SYSTEMS Corporation, and the adsorption rate was calculated by the following formula:

$$\text{Adsorption rate (\%)} = \frac{(\text{concentration in serum before incubation}) - (\text{concentration in serum after incubation})}{(\text{concentration in serum before incubation})} \times 100$$

It is noted that the concentration in serum before incubation is a value corrected for the water contained in the carrier. And the concentrations of albumin before and after incubation were measured by BCG method.

Results

<Adsorption rate of MIP-1α>

| | Adsorption rate (%) |
|---|---|
| CELLULOFINE GC-700m | 0 |
| n-Octylamine-immobilized GC-700m | 58 |

<Change of albumin concentration (g/dl)>

| | Before incubation | After incubation |
|---|---|---|
| CELLULOFINE GC-700m | 3.8 | 3.6 |
| n-Octylamine-immobilized GC-700m | 3.8 | 3.3 |

EXAMPLE 5

A hexadecylamine-immobilized carrier was obtained in the same manner as in Example 4 except that n-octylamine was replaced with hexadecylamine (Σf=7.22) and the solvent for immobilizing reaction was replaced with ethanol. The immobilized quantity of hexadecylamine was 189 μmol/dry weight of carrier (1 g).

Adsorbing experiments were performed in the same manner as in Example 4 by using this immobilized carrier, and absorption rate was calculated by measuring concentrations of MIP-1α and a change of albumin concentrations was also measured.

Results

<Adsorption rate of MIP-1α>

| | Adsorption rate (%) |
|---|---|
| Hexadecylamine-immobilized GC-700m | 99 |

<Change of albumin concentration (g/dl)>

| | Before incubation | After incubation |
|---|---|---|
| Hexadecylamine-immobilized GC-700m | 3.8 | 3.3 |

EXAMPLE 6

A n-octylamine-immobilized carrier was obtained in the same manner as in Example 4 except that CELLULOFINE GC-700m was replaced with CELLULOFINE GC-200m (molecular weight of exclusion limit for globular protein: 140,000, made by Chisso Corporation). The immobilized quantity of n-octylamine was 189 μmol/dry weight of carrier (1 g).

Adsorbing experiments were performed in the same manner as in Example 4 by using this immobilized carrier, and adsorption rate was calculated by measuring concentrations of MIP-1α and a change of albumin concentrations was also measured.

Results

<Adsorption rate of MIP-1α>

| | Adsorption rate (%) |
|---|---|
| CELLULOFINE GC-200 m | 0 |
| n-Octylamine-immobilized GC-200m | 59 |

<Change of albumin concentration (g/dl)>

| | Before incubation | After incubation |
|---|---|---|
| n-Octylamine-immobilized GC-200m | 3.8 | 3.7 |

EXAMPLE 7

A hexadecylamine-immobilized carrier was obtained in the same manner as in Example 4 except that CELLULOFINE GC-700m was replaced with CELLULOFINE GC-200m and n-octylamine was replaced with hexadecylamine and the solvent for immobilizing reaction was replaced with ethanol. The immobilized quantity of hexadecylamine was 189 μmol/dry weight of carrier (1 g).

Adsorbing experiments were performed in the same manner as in Example 4 by using this immobilized carrier, and absorption rate was calculated by measuring concentrations of MIP-1α and a change of albumin concentrations was also measured.

Results

<Adsorption rate of MIP-1α>

| | Adsorption rate (%) |
|---|---|

-continued

| Results | |
|---|---|
| <Adsorption rate of MIP-1α> | |
| | Adsorption rate (%) |
| Hexadecylamine-immobilized GC-200m | 99 |

| <Change of albumin concentration (g/dl)> | | |
|---|---|---|
| | Before incubation | After incubation |
| Hexadecylamine-immobilized GC-200m | 3.8 | 3.7 |

EXAMPLE 8

Spherical particles of a cellulose acetate were obtained by dissolving a commercially available cellulose acetate in a mixed solvent of dimethyl sufoxide and propylene glycol, forming the resulting solution into droplets by the method mentioned in Japanese Unexamined Patent Publication No. 63-117039 (vibration method) and coagulating them.

The particles were mixed with an aqueous solution of sodium hydroxide to undergo a hydrolysis reaction, giving cellulose particles (molecular weight of exclusion limit for globular protein: 30,000, hereinafter referred to as "C-1").

A hexadecylamine-immobilized carrier was obtained in the same manner as in Example 4 except that CELLU-LOFINE GC-700m was replaced with C-1 and n-octylamine was replaced with hexadecylamine and the solvent for immobilizing reaction was replaced with ethanol. The immobilized quantity of hexadecylamine was 160 μmol/dry weight of carrier (1 g).

Adsorbing experiments were performed in the same manner as in Example 4 by using this immobilized carrier, and absorption rate was calculated by measuring concentrations of MIP-1α and a change of albumin concentrations was also measured.

| Results | |
|---|---|
| <Adsorption rate of MIP-1α> | |
| | Adsorption rate (%) |
| C-1 | 0 |
| Hexadecylamine-immobilized C-1 | 99 |

| <Change of albumin concentration (g/dl)> | | |
|---|---|---|
| | Before incubation | After incubation |
| Hexadecylamine-immobilized C-1 | 3.8 | 3.6 |

COMPARATIVE EXAMPLE 2

A n-butylamine-immobilized carrier was obtained in the same manner as Example 4 except that n-octylamine was replaced with n-butylamine (log P=0.97).

Adsorbing experiments were performed in the same manner as in Example 4 by using this immobilized carrier, and absorption rate was calculated by measuring concentrations of MIP-1α and a change of albumin concentrations was also measured.

| Results | |
|---|---|
| <Adsorption rate of MIP-1α> | |
| | Adsorption rate (%) |
| n-Butylamine-immobilized GC-700m | 1 |

| <Change of albumin concentration (g/dl)> | | |
|---|---|---|
| | Before incubation | After incubation |
| n-Butylamine-immobilized GC-700m | 3.8 | 3.4 |

Comparative Example 3

A n-hexylamine-immobilized carrier was obtained in the same manner as Example 4 except that n-octylamine was replaced with n-hexylamine (log P=2.06).

Adsorbing experiments were performed in the same manner as in Example 4 by using this immobilized carrier, and absorption rate was calculated by measuring concentrations of MIP-1α and a change of albumin concentrations was also measured.

| Results | |
|---|---|
| <Adsorption rate of MIP-1α> | |
| | Adsorption rate (%) |
| n-Hexylamine-immobilized GC-700m | 6 |

| <Change of albumin concentration (g/dl)> | | |
|---|---|---|
| | Before incubation | After incubation |
| n-Hexylamine-immobilized | 3.8 | 3.3 |

As clearly shown from results given in above Examples, β2-microglobulin and chemokines, etc. in body fluid can be effectively removed by using the adsorbent of this invention wherein a compound having a log P value of 2.50 or more was immobilized on a water insoluble carrier.

The invention claimed is:

1. A method for adsorbing a chemokine in body fluid comprising: bringing an adsorbent into contact with body fluid containing the chemokine, the adsorbent comprising a water insoluble carrier and a compound having a log P value (P is a distribution coefficient in an octanol-water system) of 2.50 or more immobilized on the carrier and the chemokine belonging to the CC subfamily or CXC subfamily of chemokines, with the proviso that the body fluid does not contain a chemokine consisting of interleukin-8.

2. The method of claim 1, wherein the water insoluble carrier is a hydrophilic carrier.

3. The method of claim 1, wherein the water insoluble carrier has a porous structure.

4. The method of claim 3, wherein the water insoluble carrier has a molecular weight of exclusion limit for globular protein of from $1 \times 10^4$ to $60 \times 10^4$.

5. The method of claim 1, wherein the water insoluble carrier comprises a cellulose.

6. The method of claim 1, wherein the water insoluble carrier is a spherical hydrogel comprising a cellulose on which a compound having a log P value of 2.5 or more is immobilized and water, wherein the weight ratio of said cellulose to water is in a range of 1:9 to 3:7.

7. The method of claim 1, wherein the compound having a log P value of 2.50 or more is a compound having a hydrocarbon moiety of 8 to 18 carbon atoms.

* * * * *